United States Patent
Saveliev et al.

(10) Patent No.: US 8,538,717 B2
(45) Date of Patent: Sep. 17, 2013

(54) METHOD OF ABSORBANCE CORRECTION IN A SPECTROSCOPIC HEATING VALUE SENSOR

(75) Inventors: Alexei Saveliev, Cary, NC (US); Vilas Vyankatrao Jangale, Raleigh, NC (US); Sergeui Zelepouga, Hoffman Estates, IL (US); John Pratapas, Naperville, IL (US)

(73) Assignees: Gas Technology Institute, Des Plaines, IL (US); North Carolina State University, Raleigh, NC (US)

( * ) Notice: Subject to any disclaimer, the term of this patent is extended or adjusted under 35 U.S.C. 154(b) by 317 days.

(21) Appl. No.: 13/015,624

(22) Filed: Jan. 28, 2011

(65) Prior Publication Data

US 2012/0197575 A1 Aug. 2, 2012

(51) Int. Cl.
*G06F 19/00* (2011.01)
*G01N 21/31* (2006.01)
*G01N 21/00* (2006.01)

(52) U.S. Cl.
USPC ............................ 702/104; 356/306; 250/372

(58) Field of Classification Search
USPC .......................................................... 702/104
See application file for complete search history.

(56) References Cited

U.S. PATENT DOCUMENTS

| | | | |
|---|---|---|---|
| 3,914,604 A | 10/1975 | Hornby et al. | |
| 4,782,232 A * | 11/1988 | Bernstein et al. | 250/343 |
| 5,267,562 A | 12/1993 | Ukawa et al. | |
| 5,315,528 A | 5/1994 | L'vov | |
| 6,474,152 B1 | 11/2002 | Mullins et al. | |
| 6,917,422 B2 | 7/2005 | Samsoondar et al. | |
| 7,248,357 B2 | 7/2007 | Servaites et al. | |
| 8,139,222 B2 * | 3/2012 | Saveliev et al. | 356/432 |
| 2010/0264315 A1 | 10/2010 | Okada et al. | |

* cited by examiner

*Primary Examiner* — Bryan Bui
(74) *Attorney, Agent, or Firm* — Pauley Petersen & Erickson

(57) ABSTRACT

A method and apparatus for absorbance correction in a spectroscopic heating value sensor in which a reference light intensity measurement is made on a non-absorbing reference fluid, a light intensity measurement is made on a sample fluid, and a measured light absorbance of the sample fluid is determined. A corrective light intensity measurement at a non-absorbing wavelength of the sample fluid is made on the sample fluid from which an absorbance correction factor is determined. The absorbance correction factor is then applied to the measured light absorbance of the sample fluid to arrive at a true or accurate absorbance for the sample fluid.

11 Claims, 10 Drawing Sheets

METHOD OF ABSORBANCE CORRECTION IN A SPECTROSCOPIC HEATING VALUE SENSOR

The U.S. Government has a paid-up license in this invention and the right in limited circumstances to require the patent owner to license others on reasonable terms as provided for by the terms of Contract No. DE-EE0000556 awarded by the U.S. Department of Energy.

BACKGROUND OF THE INVENTION

1. Field of the Invention

This invention relates to a method and apparatus for the measurement of a physical property of a fluid that is dependent upon a physical characteristic of at least one functional group and is related to the quantity of that functional group in the fluid. In one aspect, this invention relates to the measurement of the heating value of a fuel gas at-line and in real-time. In one aspect, this invention relates to a method and apparatus for measuring the heating value of a combustible gaseous fuel mixture, including functional groups and molecules, using near-infrared absorption spectroscopy. In one aspect, this invention relates to a method and apparatus for correcting the measured absorbance of an absorbing fluid to produce a true or accurate absorbance.

2. Description of Related Art

In the past, the heat energy content of a combustible fluid has been determined by burning precisely defined amounts of the combustible fluid, such as natural gas, to determine the amount of energy produced from the combustion. Other methods have determined the concentration of each whole combustible compound in the mixture, defining the energy content for each whole combustible compound, and summing them to yield the heat energy content of the entire mixture.

The heat energy content of natural gas flowing through a pipeline, which natural gas typically contains methane, ethane, propane, and higher alkane hydrocarbons, frequently fluctuates, even over relatively short periods of time. Conventional methods of measurement generally require bypass flowlines or fluid extraction to provide gas samples which are then taken to a lab and burned. The temperature of the flame is then measured. Available sensors for making these measurements are primarily calorimeters and gas chromatographs. Disadvantageously, such devices, in addition to requiring the removal of samples from pipelines, have slow response times, and have high initial and maintenance costs. It is difficult to both continuously and accurately measure the energy content of natural gas in pipelines, and the lack of any convenient method for making such continuous and accurate measurements may result in improper charges during the course of a day to the disadvantage of both buyers and sellers.

One method and apparatus for addressing the need for both continuous and accurate measurement of the heat energy content of combustible gaseous fluid mixtures is described in U.S. Pat. No. 7,248,357, which is incorporated herein in its entirety by reference. As described therein, a method and system is provided for measuring the heat energy of a combustible fluid in which radiation means direct radiation through a sample of the combustible fluid, detection means detect absorbance of at least one combustible component of the combustible fluid at a selected spectral line, where there is at least one spectral line for each combustible component to be considered in the combustible fluid, calibration means calibrate the source of the radiation, storage means store a plurality of spectra of combustible gas mixtures, thereby enabling comparison of the measured absorbance spectrum to the plurality of spectra, combination means combine at least one heat energy portion factor with the absorbance at each spectral line, and summing means sum the combinations to determine the heat energy of the combustible fluid. The system continuously acquires absorption spectra from gases in the near-infrared region. The near-infrared region of the electromagnetic spectrum is particularly useful because combustible gas components, in particular methane, ethane, propane, butane, iso-butane, and hexane produce strong absorbent spectra in this spectral range. The measurement of absorption values at several predetermined wavelengths allows reconstruction of fuel composition and heating value using specially developed mathematical algorithms. The absorbance value is calculated as $$A = \ln\left[\frac{I_0}{I}\right]$$

where $I_0$ is the light intensity measured with an optical cell filled by purging gas and $I$ is the intensity of light measured with the cell filled with a fuel. Calibration (zeroing) of the system requires periodic flushing of the optical cell with a purging gas, such as nitrogen or air.

FIG. 1 is a schematic diagram of a conventional spectroscopic heating value sensor. As shown therein, the sensor comprises optical cell 10 having optical windows 11, 12 and input and output gas connectors 13 and 14. Periodic switching between fuel and purging gas flows is performed by valve 20. A stabilized radiation source 21 produces a radiation beam 22 that is passed through the cavity of the optical cell. The light exiting the optical cell through optical window 12 is dispersed by spectroscopic instrument 24 and directed to a near-infrared sensor array 25 measuring absorption at various wavelengths. The resulting signal is amplified by amplifier 26 and provided to data processor 27 for processing. When the cell is flushed with the zero-absorbing gas, light intensity from the source is acquired as a function of the wavelength and stored as the reference intensity $I_0(\lambda)$. When fuel is flowing through the cell, light is absorbed by the fuel and a spectroscopic sensor at the other end of the cell measures the absorbance of the fuel mixture as a function of wavelength $I(\lambda)$. The sensor is calibrated using absorbance spectra of fuel mixtures containing known concentrations of individual hydrocarbons at a constant pressure and temperature. During calibration, the set concentrations of known fuel mixtures are given as an input to the sensor software. Multivariate calibration techniques like Partial Components Regression (PCR) or Partial Least Squares (PLS) are utilized to form regression equations. These regression equations give individual concentrations and heating value as a function of absorbance. The heating value can be predicted directly using the regression equation or it can be calculated using the predicted concentrations.

It will be appreciated by those skilled in the art that the accuracy of the absorbance measurements depends on the stability of the reference intensity $I_0(\lambda)$ which, in turn, is affected, at least in part, by the stability of the radiation source including the radiation source temperature and radiation intensity, the spectroscopic sensor sensitivity and zero background drift, and the amplifier. U.S. Pat. No. 7,248,357 proposed to use special additional sensors and wavelength filters to independently monitor the radiation source intensity. Unfortunately, these factors cannot be completely eliminated, even by utilizing high stability (high-cost) hardware. Thus, there is a need to provide some means for correcting the errors in absorbance measurements arising as a result of these and other factors.

SUMMARY OF THE INVENTION

Accordingly, it is one object of this invention to provide a method and apparatus for improving the accuracy of absorbance measurements by a spectroscopic heating value sensor.

It is another object of this invention to provide a method and apparatus for improving the accuracy of absorbance measurements by a spectroscopic heating value sensor without the use of additional sensors and wavelength filters to independently monitor the radiation source intensity.

These and other objects of this invention are addressed by a method and apparatus for absorbance correction in which a reference radiation intensity value is determined using a non-absorbing fluid following which a sample fluid radiation intensity value is determined using a radiation absorbing sample fluid following which the sample fluid absorbance is determined. Thereafter, the radiation intensity of the radiation absorbing sample fluid is determined at a non-absorbing radiation wavelength of the radiation absorbing sample fluid from which a radiation absorbance adjustment value is determined. The difference between the sample fluid absorbance and the radiation absorbance adjustment value is determined from which the true sample fluid absorbance may then be determined.

BRIEF DESCRIPTION OF THE DRAWINGS

These and other objects and features of this invention will be better understood from the following detailed description taken in conjunction with the drawings, wherein.

DETAILED DESCRIPTION OF THE PRESENTLY PREFERRED EMBODIMENTS

Figure 1:
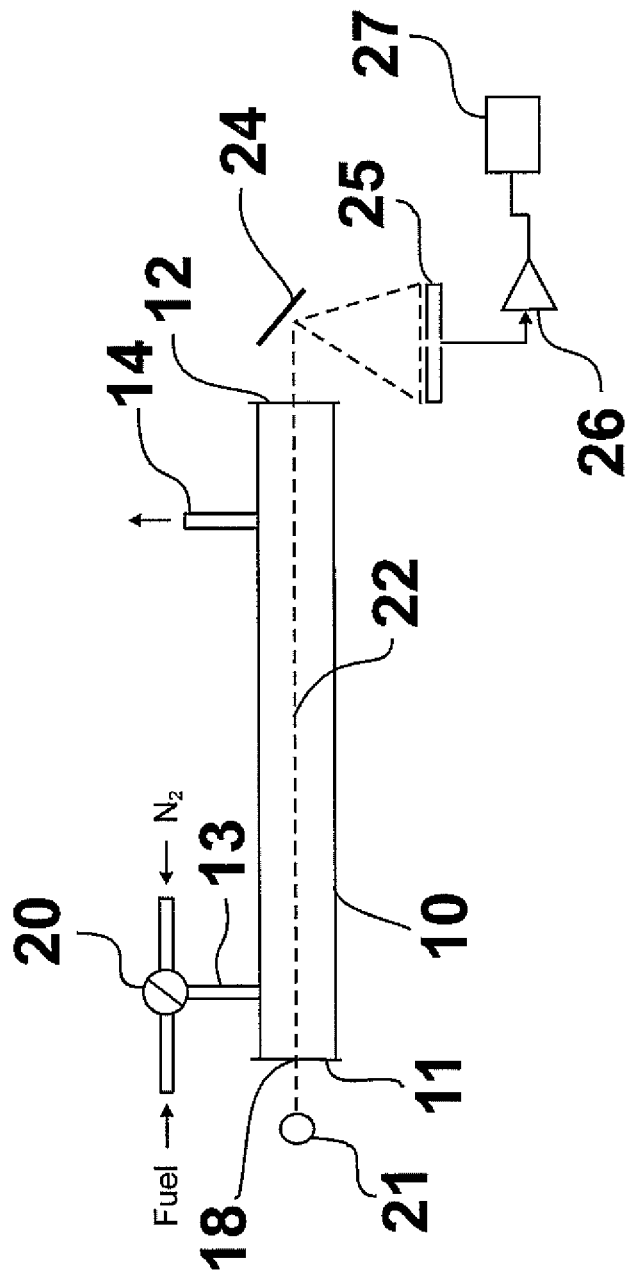
FIG. 1 is a schematic diagram of a conventional spectroscopic sensor for measuring a physical property of a fluid.
Figure 2:
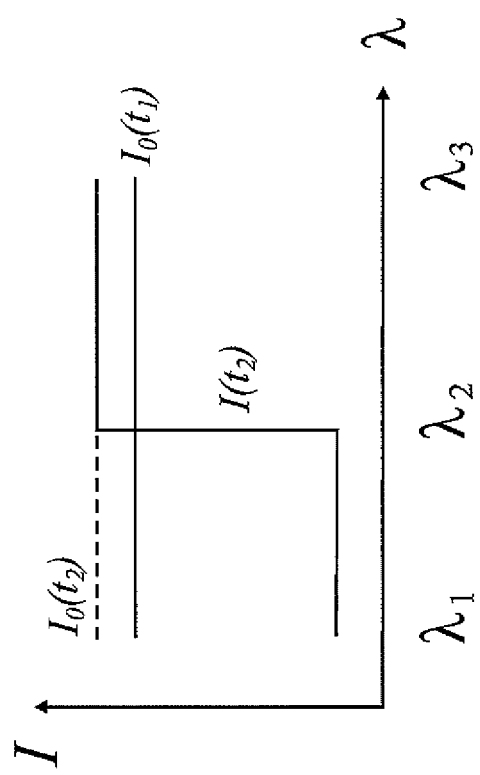
FIG. 2 is a diagram showing intensity measurements in a wavelength range.

The invention disclosed herein is a method and apparatus for absorbance correction in a spectroscopic heating value sensor which relies on the spectroscopic sensor itself to monitor variation of the reference intensity with time. Each pixel in the sensor array 25 corresponds to a narrow wavelength range. Overall, some of the pixels are in the spectrum absorbance regions of fuel mixtures while others are not. FIG. 2 shows intensity measurements in a wavelength range $\lambda 1$ to $\lambda 3$ where the absorption of radiation (light) occurs only in the region $\lambda 1$ to $\lambda 2$ ($\lambda 1 < \lambda 2 < \lambda 3$). The reference intensity is recorded at time $t_1$ and the absorbance spectrum is recorded at time $t_2$. The absorbance $A'$ at an absorbing wavelength $\lambda 1$ is given by the equation $$A' = \ln\left[\frac{I_0(t_1)}{I(t_2)}\right]$$

Ideally, $I_0(t_1) = I_0(t_2)$. However, due to the change in light source temperature, light intensity, detector sensitivity, changes in background noise and zero background drift, etc., the reference intensity gets shifted to a different value. This change in the reference intensity results in a non-zero absorbance $A^*$ at a non-absorbing wavelength $\lambda 3$ and is given by the equation $$A^* = \ln\left[\frac{I_0(t_1)}{I_0(t_2)}\right]$$

The true absorbance $A$ at wavelength $\lambda 1$ at time $t_2$ can be calculated as follows $$A = A' - A^* = \ln\left[\frac{I_0(t_1)}{I(t_2)}\right] - \ln\left[\frac{I_0(t_1)}{I_0(t_2)}\right] = \ln\left[\frac{I_0(t_2)}{I(t_2)}\right]$$

Figure 3:
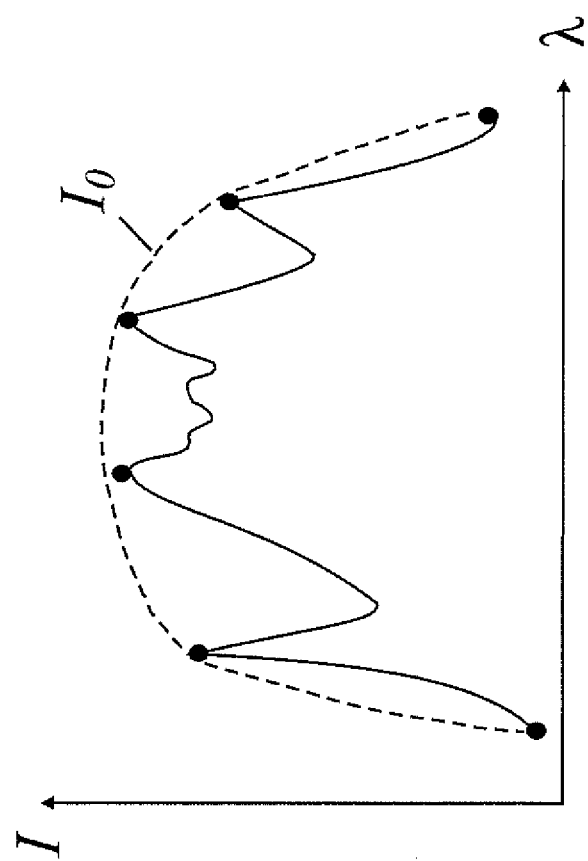
FIG. 3 is a diagram showing reconstruction of the reference intensity of the signal $I_0$ directly from the absorbance measurements using specially developed interpolation function and measurements results for $A^*(\lambda_n)$ values.

In a case of extended wavelength regions having several zero absorbance wavelengths, the resulting function $A^*(\lambda)$ can be obtained by averaging, linear or other interpolation of $A^*(\lambda_n)$ measurements obtained for individual non-absorbing wavelengths. In some cases, the reference intensity of the signal $I_0$ can be reconstructed directly from the absorbance measurements using specially developed interpolation function and measurement results for $A^*(\lambda_n)$ values as shown in FIG. 3.

Accordingly, the method of absorbance correction in accordance with this invention comprises the steps of measuring $I_0(\lambda)$ during the system purging with a non-absorbing gas, producing a reference intensity value; measuring $I(\lambda)$ for a radiation absorbing sample fluid being tested; calculating the absorbance $A'$ of the sample fluid as $$A'(\lambda) = \ln\left[\frac{I_0(\lambda)}{I(\lambda)}\right];$$

determining $A^*(\lambda_n)$ for pre-selected, non-absorbing wavelengths of the radiation absorbing sample fluid, producing at least one corrective radiation intensity value; generating function $A^*(\lambda)$ as necessary using averaging, linear interpolation, polynomial interpolation, or other interpolation methods, producing an adjusted radiation absorbance; and correcting the measured absorbance in accordance with the following formula $$A(\lambda) = A'(\lambda) - A^*(\lambda)$$

It is to be understood that the absorbance correction method of this invention may also be applied to sensors that directly measure absorbance using a light dispersion device and at least one linear array sensor having multiple pixels, with the number of pixels corresponding to the non-absorbing wavelengths. Applications of the method of this invention include measurements of fuel mixtures containing carbon dioxide and carbon monoxide, measurements of pollutant concentrations in the atmosphere, and infrared monitoring of gaseous and liquid stream compositions.

The sensor employed in the method and apparatus of this invention was tested for consistency in predicting concentrations over a period of several days during which it was determined that if calibration and measurement tests are performed on the same day, the predicted concentrations had only about a 0.5% error. However, during subsequent tests, this error was found to increase. For example, for a test conducted three days after calibration, the results had an error of about 1.35%.

Figure 4:
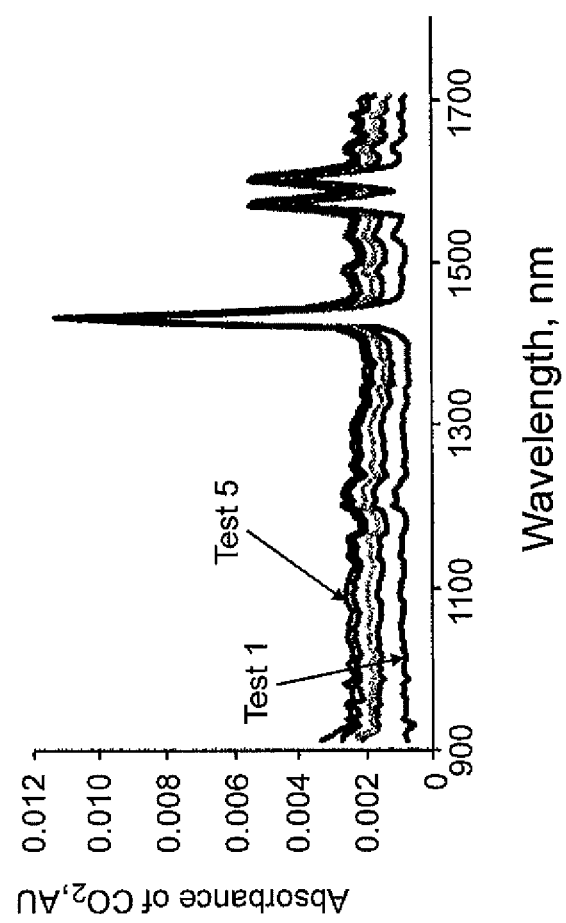
FIG. 4 is a diagram showing the absorbance spectra of pure carbon dioxide recorded in five tests performed immediately one after the other.
Figure 5:
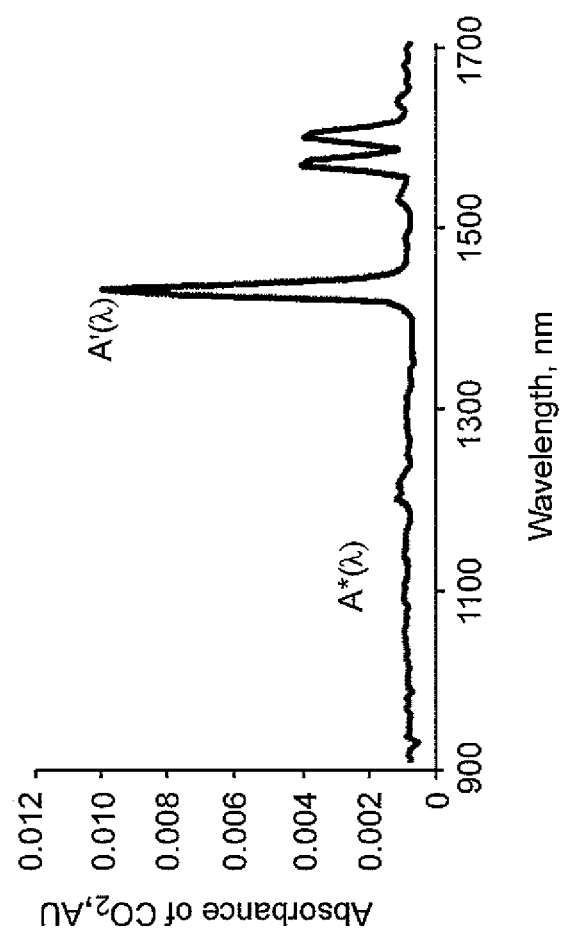
FIG. 5 is a diagram showing representative absorbance spectra of pure carbon dioxide.
Figure 6:
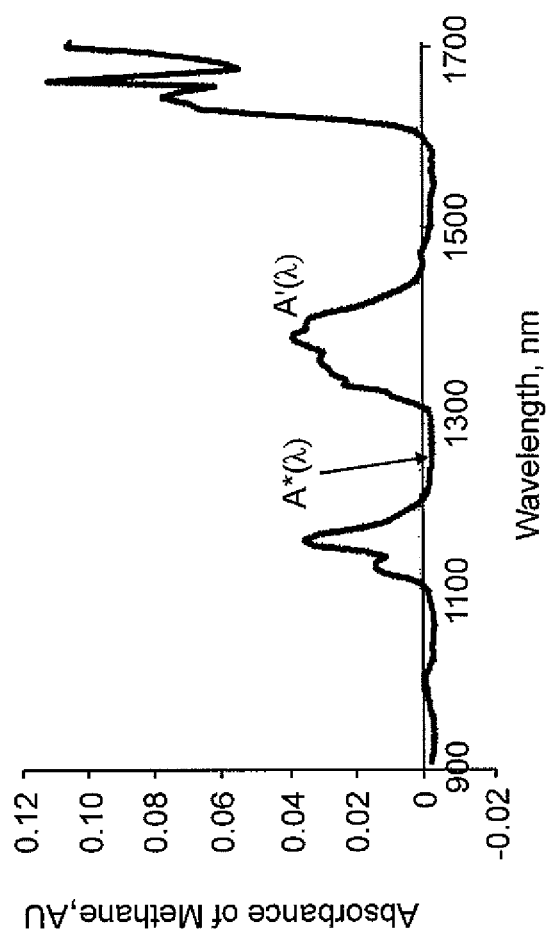
FIG. 6 is a diagram showing representative absorbance spectra of pure methane.

A series of tests were conducted using two pure species—methane and carbon dioxide. The results showed that for a constant pressure and temperature, the absorbance at a selected wavelength does not remain constant. FIG. 4 shows the absorbance spectra of pure carbon dioxide recorded in five tests performed immediately one after the other. As shown therein, there is a continuous upward shift of the absorbance spectrum as the testing progressed. FIGS. 5 and 6 show representative absorbance spectra of pure carbon dioxide and methane, respectively. As can be seen, carbon dioxide does not absorb light in the wavelength range of 900 nm to 1400 nm. However, in FIG. 4, it can be seen that there is a non-zero absorbance, $A^*$, of approximately 0.001 AU (absorbance units) over this entire wavelength range. Thus, the entire absorbance spectrum appears to be shifted up by about 0.001 AU (FIG. 5). Likely, for the same reasons, the absorbance spectrum of methane is shifted downward by about 0.003 AU (FIG. 6).

Figure 7:
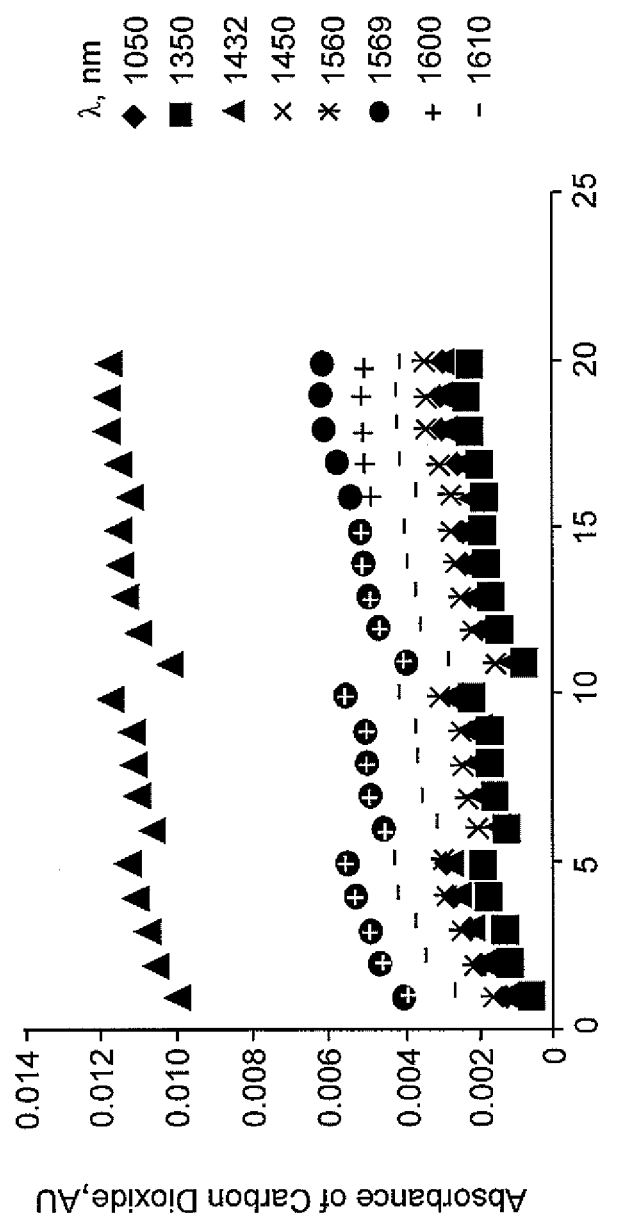
FIG. 7 is a diagram showing the absorbances at selected wavelengths for carbon dioxide.
Figure 8:
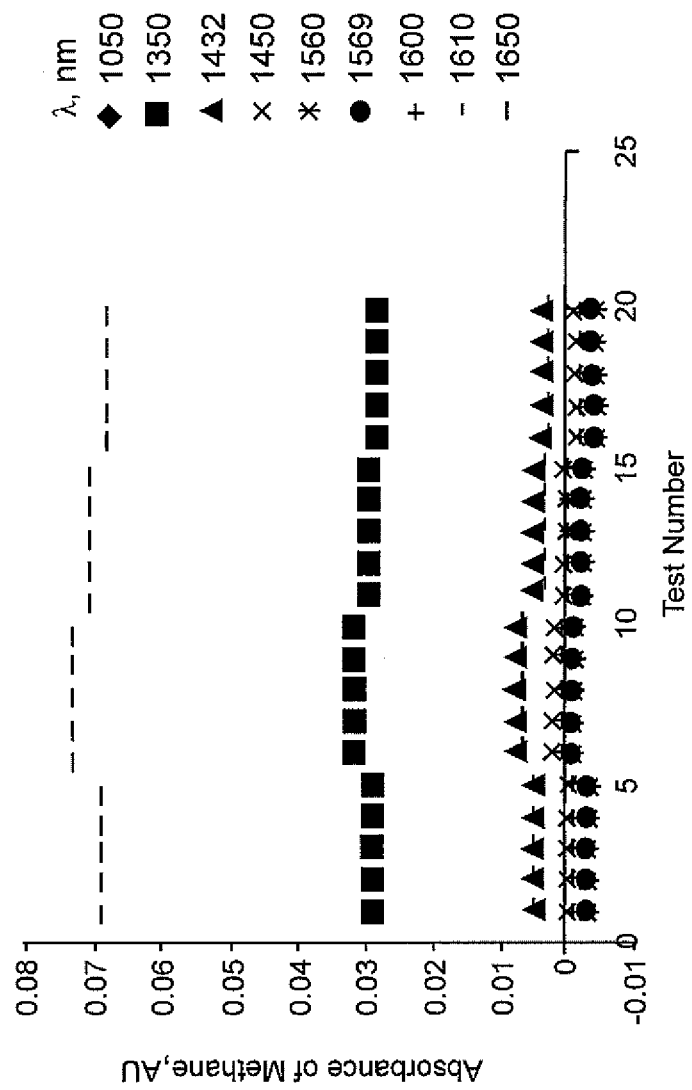
FIG. 8 is a diagram showing the absorbances at selected wavelengths for methane.

FIGS. 7 and 8 show the absorbances at selected wavelengths for carbon dioxide and methane, respectively. As can be seen, the figures clearly show small deviations in the absorbances. The spectra of both species are found to have non-zero absorbance (positive or negative) at non-absorbing wavelengths. Without wishing to be bound by any specific explanation, these false absorbances were most likely caused by instabilities of light source temperature, light intensity, detector sensitivity and zero background drift. These factors cannot be completely eliminated, even by using high stability (high-cost) hardware. Thus, in order to improve the sensor accuracy, the absorbance spectra collected from the spectroscopic sensor must be corrected mathematically before they are used in the mathematical algorithms for predicting the properties of unknown fuel mixtures or other multicomponent mixtures.

Figure 9:
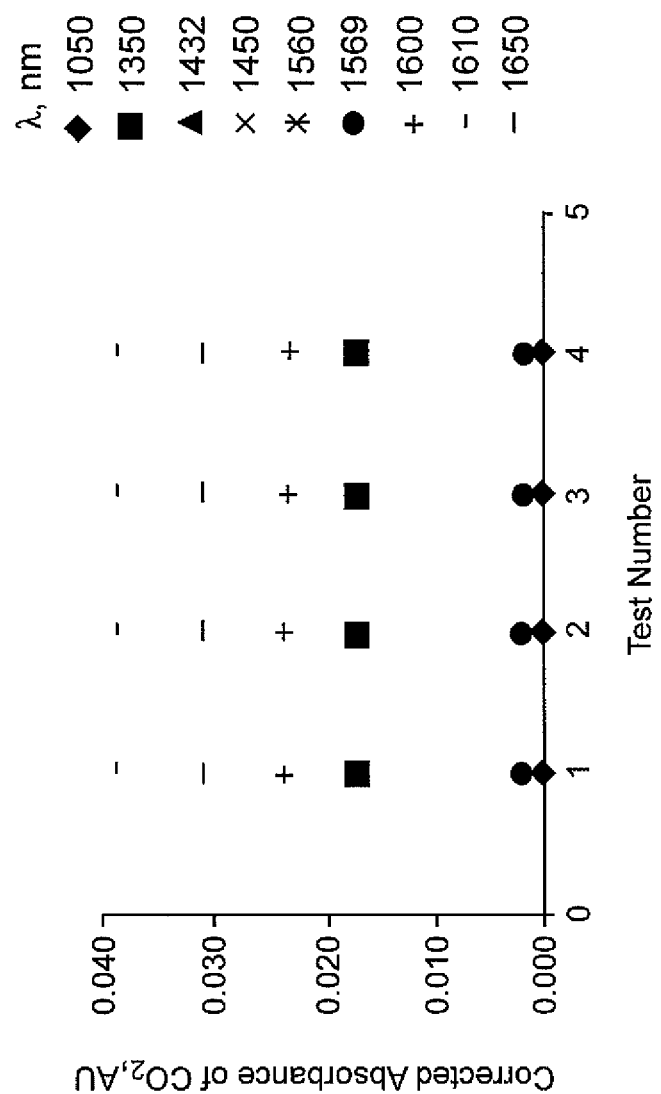
FIG. 9 is a diagram showing the corrective absorbances at selected wavelengths for carbon dioxide.
Figure 10:
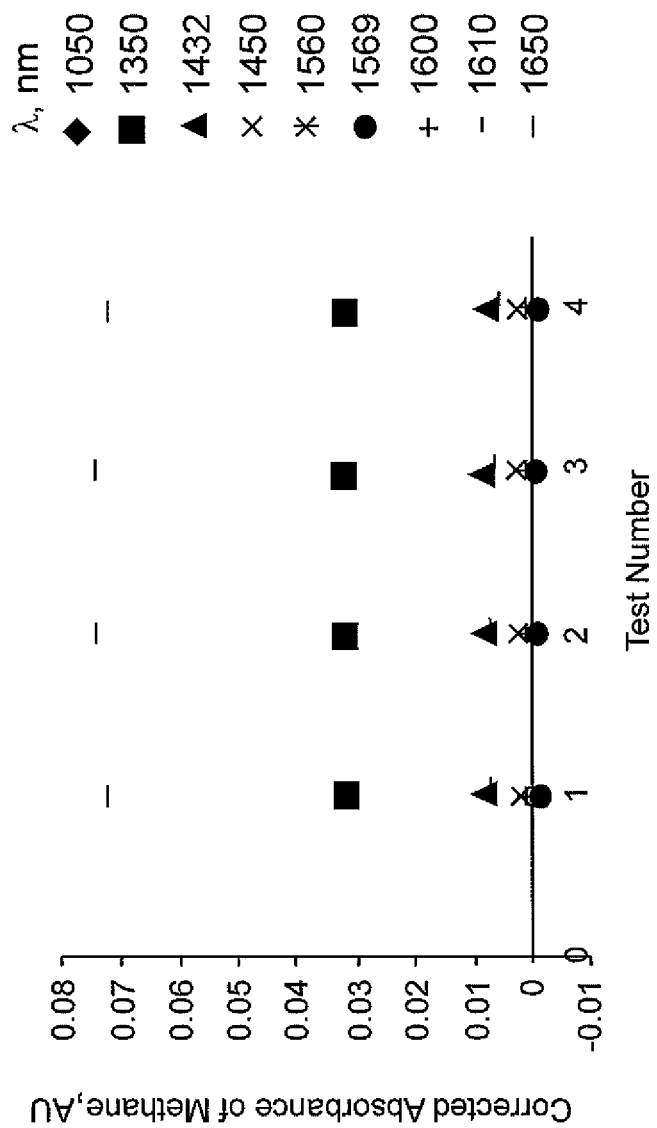
FIG. 10 is a diagram showing the corrective absorbances at selected wavelengths for methane.

The algorithm described herein above may be applied for correcting the absorbances. For example, for carbon dioxide, $A^*$ can be taken as the average of absorbances in the wavelength region of 900 nm to 1400 nm and for methane, this wavelength range may be from 1200 nm to 1300 nm and/or from 1500 nm to 1600 nm. This average absorbance may be used to calculate true absorbances at all of the wavelengths. FIGS. 9 and 10 show the corrected absorbances at selected wavelengths for carbon dioxide and methane, respectively. To obtain better accuracy, the reference intensity and background should be reacquired if the gas pressure or temperature is different than the calibration pressure and temperature.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

We claim:

1. A method for absorbance correction in a spectroscopic heating value sensor comprising the steps of:

passing radiation from a radiation source having at least one absorbing wavelength for a radiation absorbing sample fluid through a non-radiation absorbing fluid and measuring an intensity of said radiation after passing through said nonradiation absorbing fluid, producing an initial reference radiation intensity value;

passing said radiation through said radiation absorbing sample fluid and measuring said intensity of said radiation after passing through said radiation absorbing sample fluid, producing a sample fluid radiation intensity value;

passing said radiation through said radiation absorbing sample fluid and measuring said intensity at a non-absorbing wavelength of said radiation for said radiation absorbing sample fluid after passing through said radiation absorbing sample fluid, producing a correction reference radiation intensity value;

determining a measured radiation absorbance of said radiation absorbing sample fluid using said initial reference radiation intensity value and said sample fluid radiation intensity value;

determining a radiation absorbance adjustment value using said initial reference radiation intensity value and said correction reference radiation intensity value; and determining an absorbance difference between said measured radiation absorbance and said radiation absorbance adjustment value, producing a true radiation absorbance for said radiation absorbing sample fluid at said at least one radiation absorbing wavelength.

2. The method of claim 1, wherein said radiation absorbing sample fluid comprises a fuel.

3. The method of claim 1, wherein said reference radiation intensity value is monitored for changes by said spectroscopic heating value sensor.

4. The method of claim 1, wherein said radiation source is a stabilized light source selected from the group consisting of an incandescent lamp, at least one light emitting diode, and combinations thereof.

5. An apparatus for measuring a physical property of a fluid comprising:

an optical cell having a fluid inlet and a fluid outlet;

radiation means for directing radiation through said optical cell in optical communication with said optical cell;

detection means for detecting radiation absorbance by said fluid in said optical cell; and a data processor comprising correction means for applying a correction factor to said radiation absorbance to produce an accurate radiation absorbance by said fluid, wherein said correction means comprises a data processing routine in which a measured absorbance of said fluid is determined using an initial reference radiation intensity value measured for a non-absorbing fluid and a measured fluid radiation intensity value, and an adjusted radiation absorbance is determined using said initial reference radiation intensity value and a corrective radiation intensity value, said corrective radiation intensity value having been determined by passing said radiation through said fluid at a non-absorbing wavelength of said fluid from which an absorbance difference between said measured absorbance and said adjusted radiation absorbance is determined, resulting in said accurate radiation absorbance by said fluid.

6. The apparatus of claim 5, wherein said radiation means comprises at least one stabilized light source.

7. The apparatus of claim 6, wherein said at least one stabilized light source is selected from the group consisting of an incandescent lamp, at least one light emitting diode, and combinations thereof.

8. The apparatus of claim 5, wherein said radiation means comprises a radiation dispersing element disposed between said optical cell and said detection means, said radiation dispersing element adapted to disperse radiation transmitted from said optical cell to said detection means.

9. A method for absorbance correction in a spectroscopic heating value sensor comprising the steps of:
- determining a reference light intensity for a non-absorbing reference fluid;
- measuring a light absorbance of a sample fluid, producing a measured absorbance;
- determining a corrective light intensity for said sample fluid at a non-absorbing wavelength for said sample fluid, producing a corrective light intensity factor;
- determining a corrective absorbance value using said corrective light intensity factor; and
- applying said corrective absorbance value to said measured absorbance, producing a true measured absorbance.

10. The method of claim 9, wherein said sample fluid is a fuel mixture comprising a plurality of fuel components.

11. The method of claim 9, wherein said light absorbance is monitored for changes by said spectroscopic heating value sensor.

* * * * *